United States Patent [19]

Müller

[11] Patent Number: 4,526,870
[45] Date of Patent: Jul. 2, 1985

[54] DETERMINATION OF NITRATE IN WATER AND CATALYST THEREIN

[75] Inventor: Heinz-Joachim Müller, Augsburg, Fed. Rep. of Germany

[73] Assignee: Kleindienst Aquatec GmbH & Co. KG, Fed. Rep. of Germany

[21] Appl. No.: 526,510

[22] Filed: Aug. 26, 1983

Related U.S. Application Data

[62] Division of Ser. No. 416,267, Sep. 9, 1982, abandoned.

[30] Foreign Application Priority Data

Sep. 14, 1981 [DE] Fed. Rep. of Germany ....... 3136363

[51] Int. Cl.$^3$ .................... G01N 21/75; G01N 33/18
[52] U.S. Cl. .................................. 436/110; 436/164; 436/175; 502/331
[58] Field of Search ............... 436/159, 158, 115, 114, 436/110, 37, 8, 19, 175, 164; 204/1 N

[56] References Cited

U.S. PATENT DOCUMENTS

| | | | |
|---|---|---|---|
| 3,910,770 | 10/1975 | Kobylinksi et al. | 422/172 |
| 4,021,374 | 5/1977 | Petro et al. | 252/473 |
| 4,083,809 | 4/1978 | De Thomas et al. | 252/457 |
| 4,218,518 | 8/1980 | Vaseen | 429/14 |

OTHER PUBLICATIONS

Lambert et al., *Analytical Chemistry*, vol. 43, No. 7, Jun. 1971, pp. 955-957.
Armstrong, *Analytical Chemistry*, vol. 35, No. 9, Aug. 1963, pp. 1292-1294.
Perry et al. (editors), *Chemical Engineers' Handbook*, 4th edition, McGraw-Hill, Inc., 1963, pp. 18-25 and 18-26.

*Primary Examiner*—Arnold Turk
*Assistant Examiner*—Carol M. Delahunty
*Attorney, Agent, or Firm*—Ostrolenk, Faber, Gerb & Soffen

[57] ABSTRACT

A method and catalyst for the determination of nitrate in water which has been obtained by reduction of a solution of a salt of a transition metal or group VIII of the periodic system and a transition metal salt of the copper group in the presence of an acid. The nitrate determination is effected by determining the nitrate extinction of a sample of water as compared with a blank sample in the UV region at 210 nm, a part of the sample of water whose nitrate has been reduced in the presence of hydrogen with the use of the catalyst of the invention being employed as blank sample.

24 Claims, 3 Drawing Figures

DETERMINATION OF NITRATE IN WATER AND CATALYST THEREIN

This is a division of application Ser. No. 416,267, filed Sept. 9, 1982 and now abandoned.

BACKGROUND OF THE INVENTION

The present invention relates to a method of determining nitrate concentration in water and to a catalyst for this purpose which can reduce nitrates selectively in water.

During the last few years, the concentration of nitrate in surface water and ground water has continuously increased as a result of, e.g., overfertilization in agriculture. It can be noted from the Chemical Water Statistics of the Waterworks of the Federal Republic of Germany in West Berlin (edited by Dr. Gerhard Giebler, published by R. Oldenbourg, Munich 1959) that the nitrate content in ground and surface waters is in most cases 50 mg of nitrate per liter, or even more. According to the World Health Organization, the nitrate content of drinking water should not exceed 50 mg/l since with such high nitrate content there is the danger of methemoglobinemia in children. In accordance with recent findings, nitrate in combination with certain amines can form nitrosamine in the digestive tract, which substance must be considered strongly carcinogenic. It is thus necessary continuously to monitor the nitrate content of the water.

Numerous methods for determining nitrate concentration in water are known. Most determinations are based on color reactions which include either a reduction of the nitrate to nitrite, followed by diazotization to form azo dyes, or a direct reaction of the nitrate with p-fluorophenol. This last-mentioned photometric determination by fluorophenol has been introduced into the German Standardization Methods. However, this determination is very expensive and requires careful monitoring of the dosaging of the chemicals, and this method is poorly suited for a rapid continuous determination of nitrate in water.

Nitrate can also be determined by direct reaction with brucine. This method of determination, however, can be carried out only under very strict precautionary measures since brucine is a strong poison. Such a method is unsuitable for the continuous monitoring of nitrate in water.

During the last few years, ion-sensitive electrodes have also become known which permit selective determination of the nitrate ion in water. Thus, the journal Fresenius Z. Anal, Chem. 297, pages 414 and 416 (1979), describes a nitrate-ion-selective electrode having a base of cuprous neocuproine complex. However, it has been found that such ion-selective electrodes are susceptible to failure to a considerable extent so that they cannot be recommended for the continuous determination of nitrate in water.

It is also known that nitrate shows a pronounced absorption maximum in the UV region at 210 nm, which maximum could be used in general for a quantitative determination of nitrate. Since, however, surface, ground and waste water contain a large number of inorganic and organic substances which absorb in the UV region and are thus superimposed on the nitrate absorption, no method has become known up to now for a reproducible determination of nitrate via UV absorption.

The object of the present invention is, accordingly, to provide a method for determination of nitrate in water and a catalyst which can selectively reduce nitrate without at the same time reducing other entities present in the water, so that a rapid and sensitive measurement of the nitrate in water is possible by UV absorption, particularly in continuous operation.

The object of the invention is achieved by providing a catalyst for the determination of nitrate in water which is characterized by the fact that it has been obtained by reduction of a solution of a salt of a transition metal of Group VIII of the periodic system and of a transition metal salt of the copper group in the presence of an acid.

The catalyst of the invention is capable of selectively reducing nitrate in water in the presence of hydrogen, without sulfate, for instance, being reduced to sulfide, which would poison the catalyst. The catalyst can be used for the determination of nitrate in tap, ground, surface and waste waters.

The catalyst of the invention will be described in detail below.

The transition metal of Group VIII of the periodic system is preferably a metal of the platinum group, especially platinum or palladium. For the preparation of the catalyst, $(M)_2PtX_6$, $(M)_2PdX_6$, $PdX_2$ or $PtX_2$ is preferably used as transition metal salt of the platinum group, M being an alkali metal, ammonium or hydrogen and X being halogen. Ammonium hexachloroplatinate is a particularly suitable transition metal salt.

As salt of the copper group, there can be used an carbonate, nitrate or halide. Also the oxide can be used.

In the preparation of the catalyst of the invention, it is important that the transition metal of Group VIII of the periodic system and the transition metal of the copper group be used in a particular molar ratio. In preliminary investigations, it has been found that while nitrate is reduced by Raney nickel and also by platinum, nevertheless the sulfate present in the water was reduced to sulfide. Since sulfide is a catalyst poison, the Raney nickel catalyst soon becomes inactive so that it is unsuitable for the present purpose. Similar results were obtained in preliminary experiments with platinum, the platinum being rapidly inactivated even in the presence of only 10 mg/l of sulfate.

For the above reasons, the transition metal of Group VIII of the periodic system and the transition metal of the copper group are present in the catalyst in a molar ratio range of 1:8 to 8:1 and preferably 1:4 to 4:1. The molar ratio range of the transition metal of Group VIII of the periodic system to the transition metal of the copper group is, most preferably, about 1:2 to 1:4.

In the reduction of the transition metal salts to the catalyst of the invention, the acid used is generally an inorganic acid, particularly hydrochloric acid or nitric acid, or a mixture of these two acids. Instead of the direct use of transition metal salts, the transition metals can also be used in elementary form by, for instance, dissolving platinum shavings and copper wire in aqua regia.

Upon the preparation of the catalyst, the reduction of the transition metal salts takes place simultaneously, the reducing agent used being one which lies below copper in the electrochemical displacement series. Preferred reducing agents are, for instance, zinc dust or a hydrazine compound.

The catalyst is obtained by reduction at a temperature of 10°–150° C., and particularly 40°–80° C.

In accordance with a preferred embodiment, the solution of transition metal salts is applied to a support material and the reduction being carried out in the presence of the support. The solution of the transition metal salts is advisedly first subjected to a vacuum in the presence of a porous support so that the support is impregnated with the solution. This process step can be carried out, for instance, in a vacuum dessicator. Thereupon, the solution with the impregnated support material is brought back to atmospheric pressure and the transition metal salts introduced are then reduced.

As porous support materials, ceramic materials such as alumina, magnesia, silica gel or kieselguhr, activated charcoal or expanded clay enter into consideration. The support can be used in the form of Berl saddles or Raschig rings so that the catalyst applied to the support can be used in packed columns.

In accordance with another embodiment, the catalyst can also be present in the form of a coating on an electrode which is required for the liberation of hydrogen. In this case, the electrode may consist of any suitable material, for instance, carbon.

The method of the invention for the determination of nitrate in water is characterized by the fact that the nitrate extinction of a sample of water is determined as compared with a blank sample in the UV region at 210 nm, the blank sample being a part of the sample of water which is reduced in the presence of hydrogen with the use of the catalyst of the invention. The method of the invention permits a rapid, selective determination of the nitrate in water, without any substantial manipulating of the sample of water being necessary, and it is possible to avoid any substantial addition of chemicals. The method of the invention is particularly suitable for the continuous determination of nitrate and thus for the continuous monitoring of the quality of the water.

The method of the invention will be explained in further detail with reference to FIGS. 1 to 3 of the accompanying drawings.

Figure 1:
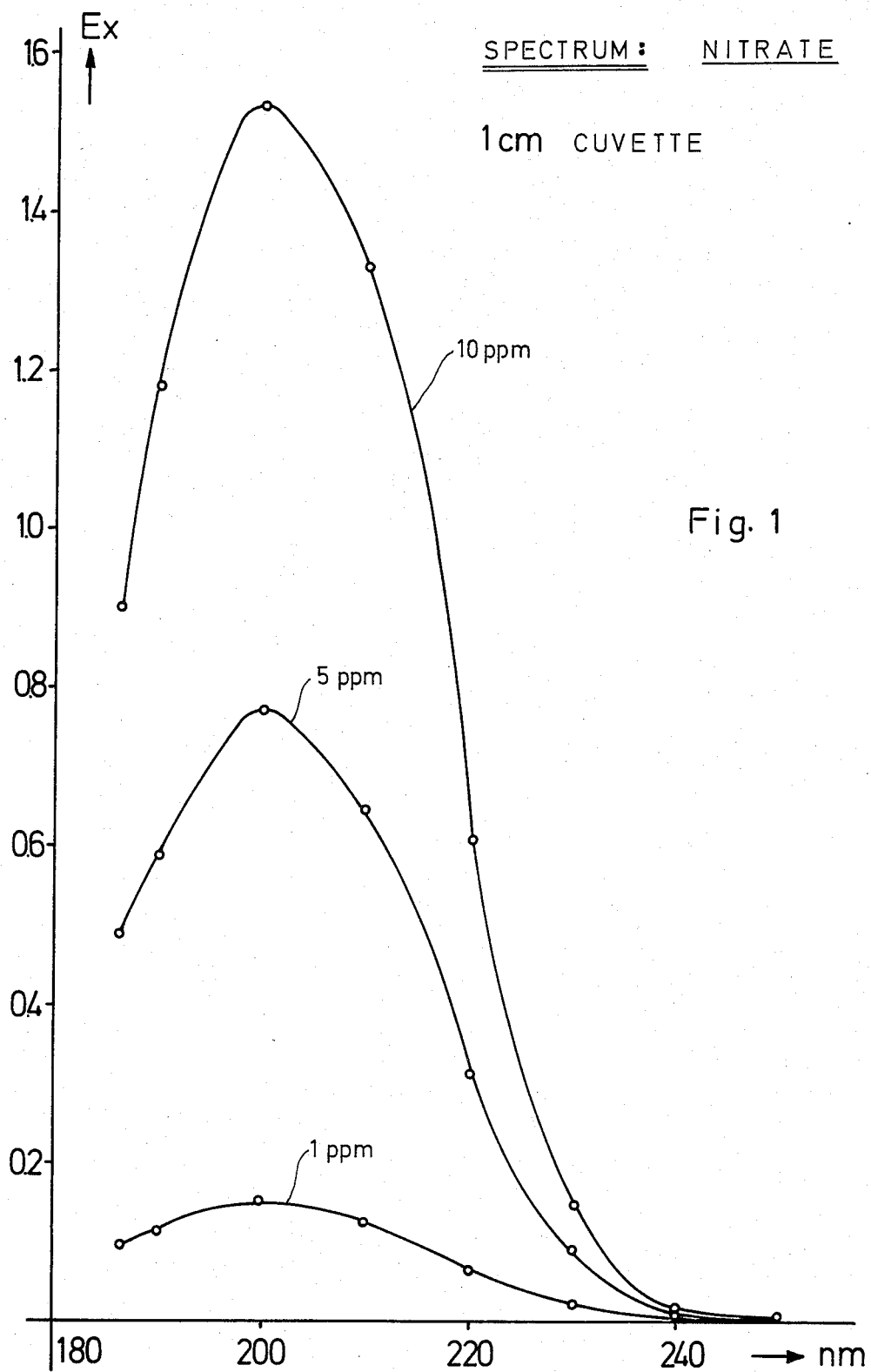
FIG. 1 shows the UV spectrum of the nitrate at different nitrate concentrations.
Figure 2:
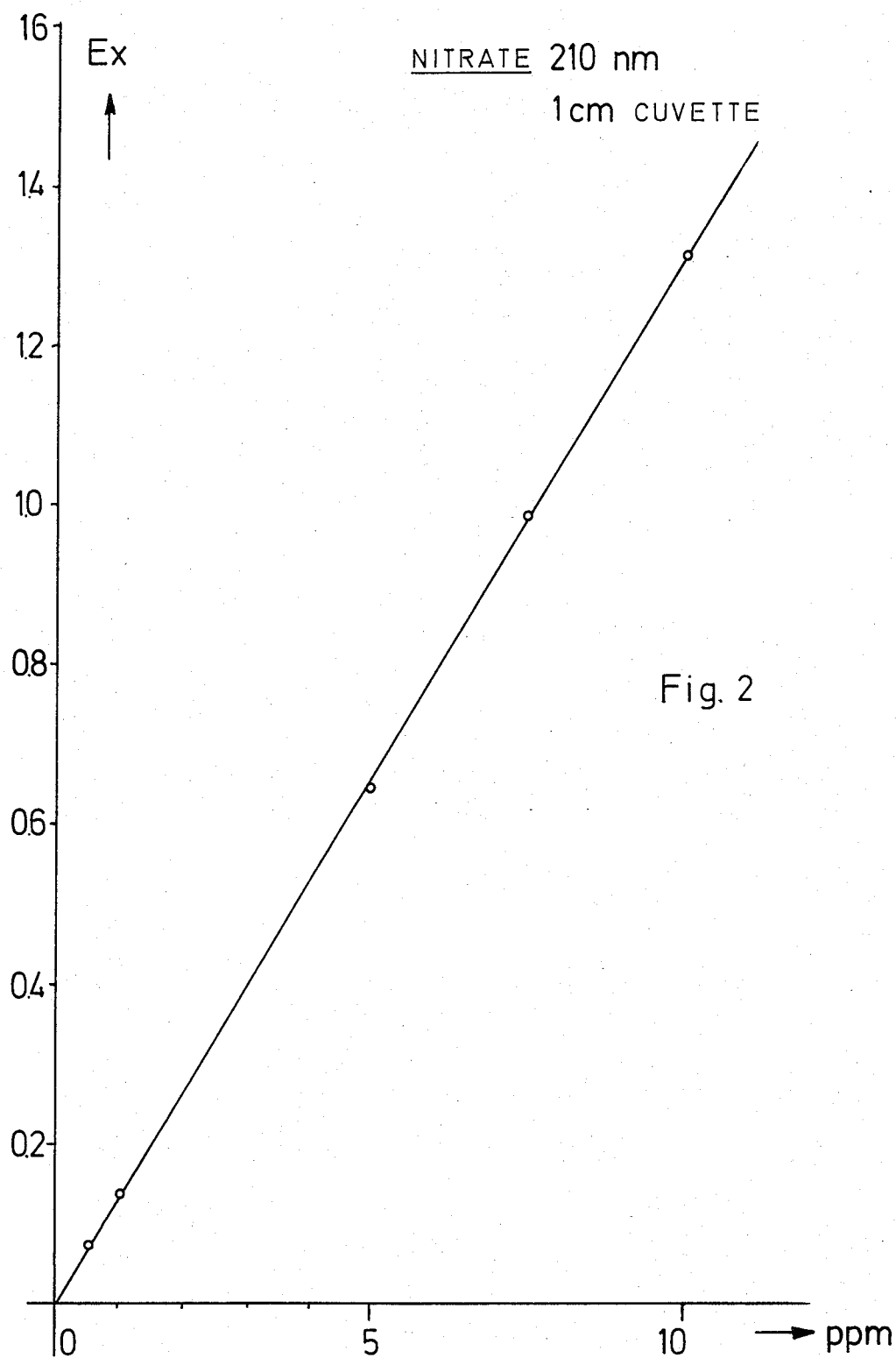
FIG. 2 shows the dependence of the nitrate extinction on the nitrate concentration at 210 nm.

As can be noted from FIG. 1, the nitrate shows a pronounced absorption maximum in the UV region, in particular at 210 nm. As can furthermore be noted from FIG. 2, there is a precisely linear relationship between the extinction of the nitrate at 210 nm and the nitrate concentration, so that the light attenuation of the nitrate in the UV region is suitable for the quantitative determination of the nitrate in the ppm range.

By a selective reduction of the nitrate in a part of the water sample, there is obtained a blank sample which differs from the water sample to be measured solely by the fact that the absorption band of the nitrate has disappeared as a result of the reduction of the nitrate, so that a precisely comparable blank sample is available. The nitrate measurement values obtained by the method of the invention showed good reproducibility, as was verified by comparison with a modified brucine measurement method.

When carrying out the nitrate reduction, the hydrogen may be supplied from a separate source. However, the hydrogen is preferably obtained electrolytically from the water so that no separate dosaging of chemicals is necessary.

The catalyst used for the nitrate reduction can be present as catalyst sponge in a fluidized bed through which the part of the sample of water to be reduced is conducted. In accordance with a preferred feature of the invention, the nitrate reduction is carried out with a catalyst applied to a support which is introduced, for instance, into a packed column. The water to be reduced is then conducted through such a packed column charged with the catalyst. In addition, the reduction can also be carried out by the use of an electrode required for the development of hydrogen which is coated with catalyst material.

In order to form the blank sample, the sample of water is preferably conducted in countercurrent to the hydrogen. In this case, the sample of water should be reduced for up to ten minutes, and particularly 2 to 6 minutes, in the presence of hydrogen and the catalyst. The nitrate reduction can be carried out at 5° to 30° C., and preferably at room temperature.

Figure 3:
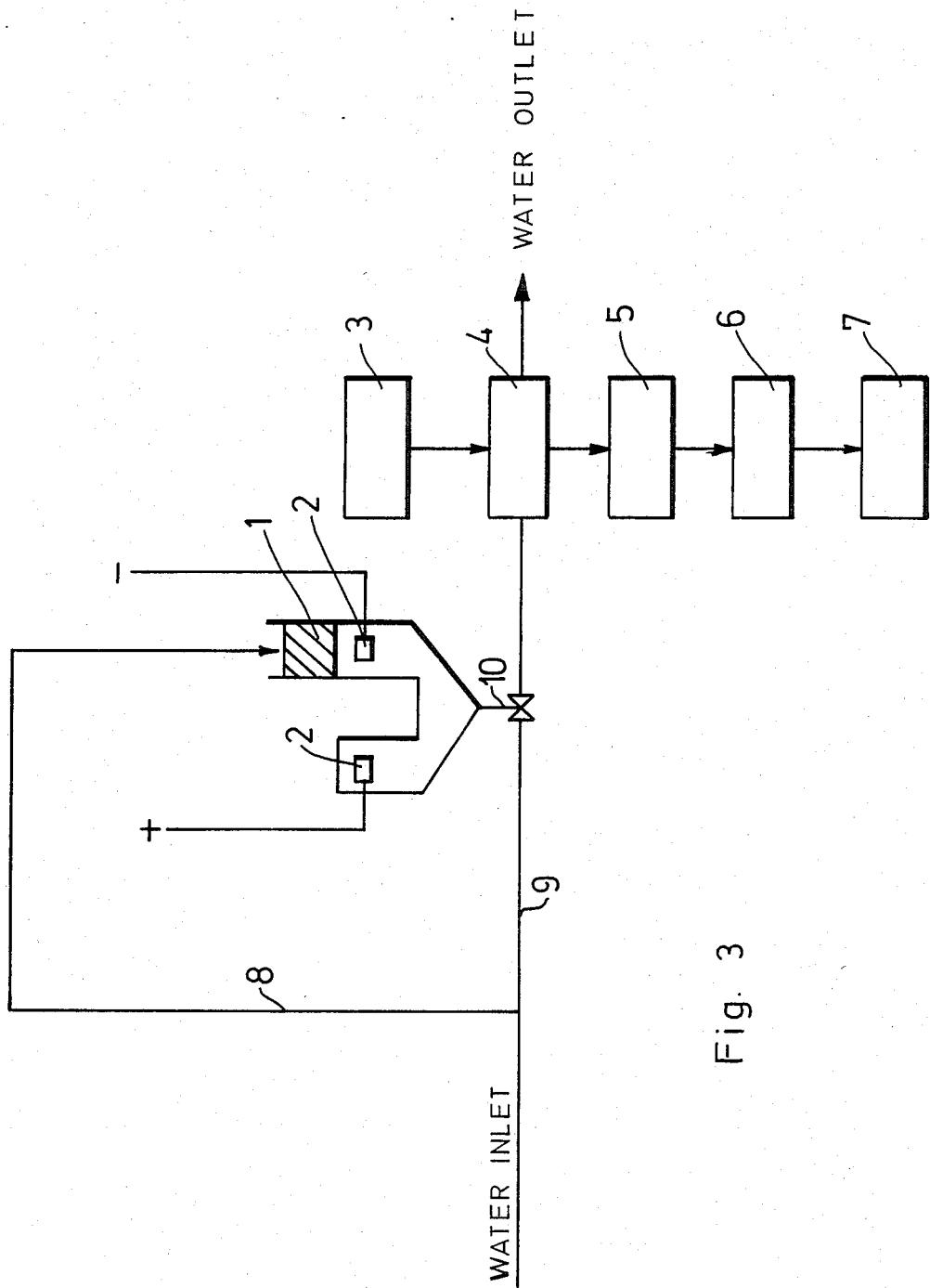
FIG. 3 is a diagrammatic showing of the course of the process.

One suitable embodiment of the method of carrying out the invention is shown in FIG. 3.

A sample of water is conducted via a conduit 9 into a quartz cell 4 equipped within a photometer. A part of the sample of water is diverted by a conduit 8 to a packed column 1 which is filled with the catalyst applied to a support material. The water flows through the packed column with a velocity, for instance, of 100 to 300 ml per hour, and the hydrogen which is produced electrolytically by the electrodes 2 ascending simultaneously in countercurrent. The amount of hydrogen introduced is advisedly about 40 to 80 ml/minute. The sample which has been reduced in this manner flows through a conduit 10 into cell 4 and serves as the blank sample. The photometer, in addition to containing the quartz cells 4, also contains a UV lamp 3, a detector 5, a memory 6 and a display unit 7. As quartz cells, there can be used continuous-flow cells so that continuous operation is possible.

The invention will be explained in further detail by the following examples.

EXAMPLE 1

444 mg of $(NH_4)_2PtCl_6$ and 269 mg of $CuCl_2$ are dissolved in a mixture of 40 ml of 37% hydrochloric acid and 80 ml of water. 2 g of Zn dust are added while stirring with a magnetic stirrer. After the liberation of gas has ceased, the cementate is washed free of chloride and used as the catalyst in a fluidized bed.

EXAMPLE 2

444 mg of $(NH_4)_2PtCl_6$ and 269 mg of $CuCl_2$ were dissolved in a mixture of 40 ml of hydrochloric acid (37%) and 80 ml of water. 10 g of expanded clay were impregnated with this solution in vacuum (vacuum dessicator). After expansion to atmospheric pressure, the prepared expanded clay was introduced into a mixture of 40 ml of 37% hydrochloric acid and 80 ml of water. The reduction was then effected by the addition of 2 g of Zn dust. The catalyst, applied to the support material, was introduced into a packed column.

EXAMPLE 3

1 g of platinum shavings and 1.5 g of copper wire were dissolved in aqua regia. Thereupon evaporation was effected practically to dryness followed by extraction with 37% hydrochloric acid followed again by evaporation. This process was repeated until no nitrous vapors were obtained, as was the case after four evaporations. After the dissolving of the residue in a mixture of 40 ml of 37% hydrochloric acid and 80 ml of water, reduction was effected by means of 2 g of Zn dust.

EXAMPLE 4

In the following example, the decomposition of nitrate was examined as a function of the molar ratio of platinum to copper in the cementate. Tap water containing 15 mg/l of sulfate was used as model water and it was treated with sodium nitrate so as to obtain 10 mg of nitrate per liter. Portions of 100 ml of water were gassed for 5 minutes, with agitation, by hydrogen, in a 200 ml wash bottle in the presence of the catalyst material which had been freed of the hydrogen present as a result of the conditions of manufacture, by means of a sodium nitrate solution. The feed of the hydrogen gas amounted to about 60 ml/minute. The decrease in the nitrate was determined by the extinction in the UV region at 210 nm and, furthermore, as reference, by a modified brucine method.

TABLE I

| Molar ratio Pt:Cu | 1st batch | 2nd batch | 3rd batch | $NO_3^-$ Ex 210 $c/c^o$ | $NO_3^-$ Brucine $c/c^o$ |
| --- | --- | --- | --- | --- | --- |
| 1:2 | 0.025 | 0.033 | 0.012 | 0.01 | 0.00 |
| 2:1 | 0.050 | 0.220 | 0.750 | 0.57 | 0.54 |
| 3:1 | 0.013 | 0.350 | 0.980 | 0.74 | 0.70 |
| 3:2 | 0.018 | 0.195 | 0.630 | 0.48 | 0.62 |
| 1:3 | 0.065 | 0.078 | 0.069 | 0.05 | 0.04 |

It can be noted from the above table that a catalyst having a molar ratio of platinum to copper of 1:2 or 1:3 gives the best results since the nitrate is removed practically down to the limit of detection. With the three other platinum/copper catalysts, increasingly incomplete degradation of the nitrate is observed, due to the fact that the sulfate present is reduced to the sulfide by these catalysts, the sulfide then poisoning the catalyst. From the last two columns of Table I it is clear that the results obtained by the brucine method show good agreement with the results obtained by the method of the invention.

EXAMPLE 5

In the present experiment, the long-time behavior of the catalyst applied to support material in a packed column was examined. A burette with frit ($\phi=2$ cm) introduced therein was filed up to a height of 50 cm with a support catalyst prepared in accordance with Example 2 and gassed from the bottom with about 60 ml of $H_2$/minute. Tap water, to which 10 mg of nitrate per liter had been added, was conducted in countercurrent through the material with a velocity of flow of 200 ml/hour.

TABLE II

| Duration in hours Ex. 210 | Extinction 210 nm Ex. 210 | $c/c^o$ Extinction 210 nm Ex. 210 | $c/c^o$ Brucine |
| --- | --- | --- | --- |
| 4 | 0.033 | 0.03 | 0.03 |
| 8 | 0.068 | 0.05 | |
| 12 | 0.012 | 0.01 | |
| 16 | 0.055 | 0.04 | 0.06 |
| 20 | 0.045 | 0.04 | |
| 24 | 0.063 | 0.05 | |
| 28 | 0.035 | 0.03 | 0.10 |
| 32 | 0.048 | 0.04 | |
| 36 | 0.042 | 0.03 | |
| 40 | 0.059 | 0.05 | 0.05 |

From the above experimental results, it is clear that the nitrate is practically completely reduced by the catalyst of the invention even upon longer periods of treatment since the extinction values indicated lie at the limit of detection. Furthermore, the last two columns of Table II show the good agreement between the measurement results obtained on the one hand by the method of the invention; as in Table II, c is the nitrate concentration after catalyst treatment and $c^o$ is the initial nitrate concentration and on the other hand by the modified brucine method.

COMPARATIVE TEST 1

In this comparative test, the catalytic properties of Raney nickel were examined. Distilled water containing 10 mg of nitrate per liter was used as a model solution. After contact times of 30 to 60 minutes, no nitrate could be detected. Furthermore, it was observed that even upon gasification with hydrogen the reductive power of the material decreased.

In tests with tap water, however, it was found, that on the one hand, the Raney nickel was inactivated faster and, on the other hand, larger quantities of Raney nickel were necessary for the reduction of the same amount of nitrate as in the distilled water. The reason for the inactivation was that sulfate was present in the tap water and it was reduced to sulfide which acted as catalyst poison.

COMPARATIVE TEST 2

Tests similar to those employed in comparative example 1 were carried out with the use of platinum sponge. Substantially the same results were obtained as when using Raney nickel except that no inactivity arose in the absence of sulfate. This means that upon gasification with hydrogen continuous reduction of the nitrate takes place. However, in the presence of sulfate the platinum is rapidly inactivated even at concentrations as low as about 10 mg/l.

What is claimed is:

1. A method of determining nitrate in water comprising:

dividing a nitrate containing water sample into first and second portions;

reacting the first portion with gaseous hydrogen in the presence of a catalyst at a temperature of 5°–30° C. until the absorption caused by the nitrate in the ultraviolet spectrum at 210 nm has disappeared, the catalyst being the product of the reduction of a solution of a compound of a transition metal of the platinum group and a compound of a transition metal of the copper group in the presence of an acid, the catalyst containing the transition metal of the platinum group and the transition metal of the copper group in a molar ratio in the range from 1:8 to 8:1, whereby the nitrate is selectively reduced without the other entities present in the water being reduced at the same time; and comparing the extinction of the second portion with the extinction of the reacted first portion at 210 nm in the ultraviolet range.

2. A method according to claim 1, wherein the copper group metal is in the form of an oxide, carbonate, nitrate or halide of copper.

3. A method according to claim 1, wherein the range of molar ratio of the transition metal of the platinum group to the transition metal of the copper group is about 1:2 to 1:4.

4. A method according to claim 1, wherein the acid is an inorganic acid.

5. A method according to claim 1, wherein the reacting of the first portion is effected by conducting the first portion through a fluidized bed of the catalyst.

6. A method according to claim 1, wherein the first portion is reacted by contact with an electrode for the liberation of hydrogen which is coated with the catalyst.

7. A method according to claim 1, wherein the transition metal of the platinum group and the transition metal of the copper group are in a molar ratio in the range of 1:4 to 4:1.

8. A method according to claim 1, wherein the transition metal of the platinum group is platinum or palatium and the transition metal of the copper group is copper.

9. A method according to claim 1, wherein the first portion is conveyed through a packed column charged with the catalyst applied to a support at a speed from 100 to 300 ml per hour while hydrogen is passed through the packed column countercurrent to the first portion at a speed of 40 to 80 ml per minute.

10. A method according to claim 1, wherein the transition metal of the platinum group is in the form of $(M)_2PtX_6$, $(M)_2PdX_6$, $PdX_2$ or $PtX_2$, in which M is an alkali metal, $NH_4^+$ or hydrogen and X is halogen.

11. A method according to claim 10, wherein M is ammonium and X is chloride.

12. A method according to claim 1, wherein the catalyst has been obtained by reduction with a reducing agent which is below copper in the electrochemical displacement series.

13. A method according to claim 12, wherein the reducing agent is zinc dust or a hydrazine compound.

14. A method according to claim 1, wherein the catalyst has been obtained by reduction at 10° to 150° C.

15. A method according to claim 14, wherein the catalyst has been obtained by reduction at 40°–80° C., the acid is HCl, $HNO_3$, or mixtures thereof, and the molar ratio of transition metal of the platinum group to transition metal of the copper group is in the range of 1:4 to 4:1.

16. A method according to claim 1, wherein the first portion is reduced for up to ten minutes.

17. A method according to claim 16, wherein the first portion is reduced for up to 2 to 6 minutes.

18. A method according to claim 1 wherein the catalyst is carried by a support.

19. A method according to claim 18, wherein the catalyst has been obtained by subjecting a solution of transition metal salts in the presence of a porous support to a vacuum, returning the support prepared in this manner to atmospheric pressure and reducing the transition metal salts introduced.

20. A method according to claim 18, wherein the first portion is conducted through a packed column which is charged with the catalyst applied to a support.

21. A method according to claim 18, wherein the porous support is a ceramic material, activated charcoal or expanded clay.

22. A method according to claim 21, wherein the support is present in the form of Berl saddles or Raschig rings.

23. A method according to claim 18, wherein the support is present in the form of an electrode on which a coating of the catalyst material has been applied.

24. A method according to claim 23, wherein the electrode is carbon.

* * * * *